US007544325B2

(12) United States Patent
Hill et al.

(10) Patent No.: US 7,544,325 B2
(45) Date of Patent: Jun. 9, 2009

(54) BIER VESSEL HIGH-SPEED BIOLOGICAL INDICATOR SHUTTLING SYSTEM

(75) Inventors: Aaron L. Hill, Erie, PA (US); Jeffrey A. Goughnour, Erie, PA (US); Leslie M. Logue, Edinboro, PA (US); Frank E. Dougherty, Fairview, PA (US)

(73) Assignee: American Sterilizer Company, Mentor, OH (US)

( * ) Notice: Subject to any disclaimer, the term of this patent is extended or adjusted under 35 U.S.C. 154(b) by 814 days.

(21) Appl. No.: 10/987,704

(22) Filed: Nov. 12, 2004

(65) Prior Publication Data

US 2005/0112026 A1    May 26, 2005

Related U.S. Application Data

(60) Provisional application No. 60/525,069, filed on Nov. 25, 2003.

(51) Int. Cl.
*G01N 33/00* (2006.01)
(52) U.S. Cl. ............................ 422/58; 422/68.1; 435/31
(58) Field of Classification Search .................. 422/58; 435/31
See application file for complete search history.

(56) References Cited

U.S. PATENT DOCUMENTS

| 5,591,396 | A | 1/1997 | Chiffon et al. .............. 422/26 |
| 5,858,304 | A | 1/1999 | Breach ......................... 422/26 |
| 5,906,800 | A | 5/1999 | Napierkowski et al. ..... 422/298 |
| 6,001,305 | A | 12/1999 | Mueller ......................... 422/26 |
| 2002/0160440 | A1* | 10/2002 | McDonnell et al. ........... 435/31 |
| 2003/0012689 | A1 | 1/2003 | Caputo et al. ................. 422/32 |
| 2004/0265945 | A1* | 12/2004 | Morrison ....................... 435/31 |

OTHER PUBLICATIONS

Pharmaceutical Systems, Inc. advertisement information sheet entitled: "VHyPer™ Product Specifications," 1 page. (This advertisement was known to the Applicants prior to the filing date of Applicant's U.S. Appl. No. 60/525,069).

* cited by examiner

*Primary Examiner*—Jill Warden
*Assistant Examiner*—Christine T Mui
(74) *Attorney, Agent, or Firm*—Kusner & Jaffe; Michael A. Centanni

(57) ABSTRACT

An apparatus for testing the efficacy of a sterilizing environment on a test indicator, comprising a test chamber, a loading chamber adjacent to the test chamber and an opening connecting the test chamber to the loading chamber. A movable gate mechanism has a first position closing the opening and isolating the test chamber from the loading chamber, and a second position wherein the opening connects the test chamber to the loading chamber. A system is connected to the inlet port and the outlet port of the test chamber for supplying a sterilant vapor to the test chamber to establish a sterilizing environment in the test chamber. An indicator holder is operable to move a test indicator from the loading chamber into and out of the test chamber when the gate mechanism is in the second position.

20 Claims, 10 Drawing Sheets

BIER VESSEL HIGH-SPEED BIOLOGICAL INDICATOR SHUTTLING SYSTEM

This application claims the benefit of U.S. Provisional Application No. 60/525,069, filed on Nov. 25, 2003.

FIELD OF THE INVENTION

The present invention relates generally to the art of sterilization and decontamination, and more particularly to a system for evaluating biological indicators that are used to determine the efficacy of methods of sterilization.

BACKGROUND OF THE INVENTION

Biological indicators are used to determine the efficacy of methods of sterilizing articles. Biological indicators contain specific amounts of microorganisms and are designed to be placed within a sterilization device to determine whether such device is operating properly. In this respect, after a sterilization process, the biological indicators are removed and assayed to determine whether a sufficient reduction in the number of microorganisms has taken place. The "D" value of a sterilant is defined as the time increment necessary for one log reduction in bio-burden.

Biological Indicator Evaluator Resistometers (BIER's) have been developed to test such biological indicators. Basically, a biological indicator is placed within a BIER vessel and a sterilization cycle is run to expose the biological indicator to a sterilant for a predetermined period of time. Ideally, the biological indicator is exposed to a predetermined concentration of sterilant for a predetermined exposure time. However, in most BIER systems, there are "transient" periods preceding and following the desired exposure time, as the concentration of the sterilant within the vessel builds up (typically from a zero concentration) to the desired exposure concentration preceding the exposure period, and then drops off from the predetermined exposure concentration back to zero following the exposure time.

For situations where the "D" value is defined in minutes and hours, the effect of the transient periods of the BIER vessel cycle does not create significant errors in the overall measurement of the "D" value. However, in situations where a strong sterilant or a weak biological indicator is used, the "D" value may be relatively short, and in some cases, fractions of a second. In these cases, the effects of the "transient portion" of the BIER vessel operating cycle can create significant errors in the "D" value measurement. For sterilants that have low "D" values, or for relatively weak biological indicators, the transient portion of the operating cycle must be minimized or eliminated.

The present invention overcomes this and other problems and provides a BIER vessel system capable of exposing biological indicators to relatively short exposure periods.

SUMMARY OF THE INVENTION

In accordance with a preferred embodiment of the present invention, there is provided an apparatus for testing the efficacy of a sterilant vapor, comprising a test chamber having an inlet port and an outlet port. An indicator-loading chamber is adjacent and connectable to the test chamber. A movable valve element is disposed between the test chamber and the loading chamber. The valve element is movable between a first position isolating the test chamber from the loading chamber and a second position opening the test chamber to the loading chamber. Means are provided for reciprocally moving an indicator holder between a loading position in the loading chamber and a test position in the test chamber. A sterilant vapor supply system is connected to the inlet port and the outlet port of the test chamber for supplying a sterilant vapor to the test chamber to establish a sterilizing environment in the test chamber. A controller is operable to cause the valve element to move from the first position to the second position and the moving means to move the specimen holder to the test position for a predetermined period of time and to move the valve element to the first position when the indicator holder is in the loading position.

In accordance with another aspect of the present invention, there is provided an apparatus for testing the efficacy of a sterilizing environment on a test indicator, comprising a test chamber, a loading chamber adjacent to the test chamber and an opening connecting the test chamber to the loading chamber. A movable gate mechanism has a first position closing the opening and isolating the test chamber from the loading chamber, and a second position wherein the opening connects the test chamber to the loading chamber. A system is connected to the inlet port and the outlet port of the test chamber for supplying a sterilant vapor to the test chamber to establish a sterilizing environment in the test chamber. An indicator holder is operable to move a test indicator from the loading chamber into and out of the test chamber when the gate mechanism is in the second position.

In accordance with another aspect of the present invention, there is provided an apparatus for testing the efficacy of a sterilizing environment on a test indicator, comprising a vessel having a sterilization chamber and a housing having a loading chamber. The housing is adjacent to the vessel. A passage connects the sterilization chamber to the loading chamber. A movable gate mechanism has a first position closing the passage and isolating the test chamber from the loading chamber, and a second position wherein the passage connects the test chamber to the loading chamber. An indicator holder is operable to move a test indicator from the loading chamber into and out of the test chamber when the gate mechanism is in the second position. A sterilant vapor circulation system is provided for supplying a sterilant vapor. The circulation system has a first path through the sterilization chamber, a second path through the loading chamber, and a purge system for directing a purging gas through the loading chamber. Means are provided for selectively controlling the flow of the sterilant vapor and the purge gas through the first and second paths.

It is an advantage of the present invention to provide a BIER vessel system having a high-speed biological indicator shuttle system that significantly reduces the "transient periods" wherein a biological indicator is exposed to the sterilant.

It is another advantage of the present invention to provide a system as described above that has operating cycles that range from a few seconds to several hours.

Another advantage of the present invention is to provide a system as described above that can rapidly insert and remove a biological indicator from a relatively large chamber having a sterilant therein.

It is a further advantage of the present invention to provide a system as described above wherein exposure to a sterilant is abruptly terminated upon removal of the indicator from the sterilization chamber.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF PREFERRED EMBODIMENT

Figure 1:
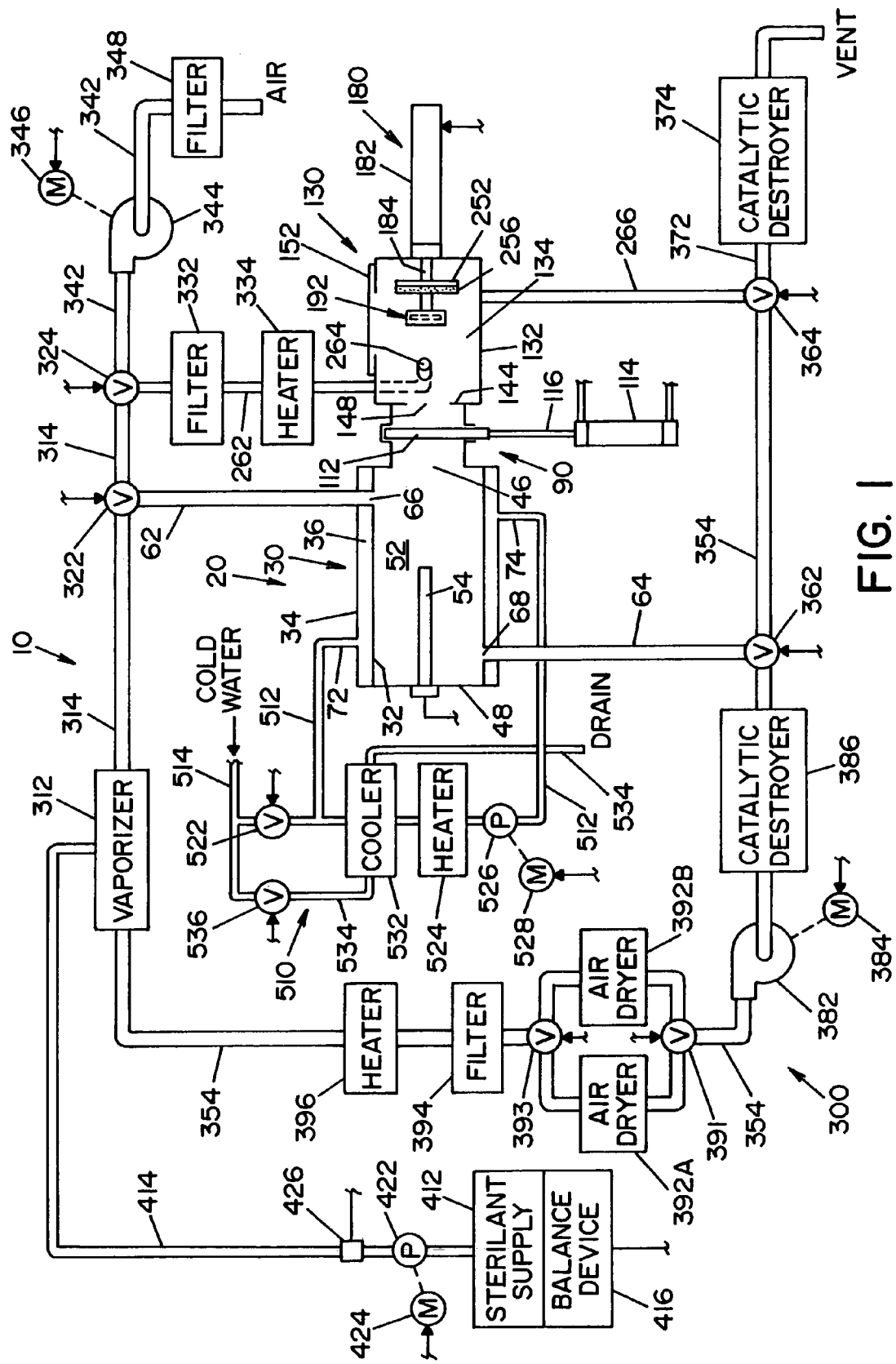
FIG. 1 is a schematic view of a BIER vessel and high-speed biological indicator shuttle system, illustrating a preferred embodiment of the present invention.

Referring now to the drawings wherein the showings are for the purpose of illustrating a preferred embodiment of the invention only, and not for the purpose of limiting same, FIG. 1 shows a system 10 for evaluating the efficacy of biological indicators when exposed to a sterilant. System 10 is comprised of a BIER vessel assembly 20, a sterilant generating and circulating system 300 and a vessel heating/cooling system 510.

Figure 2:
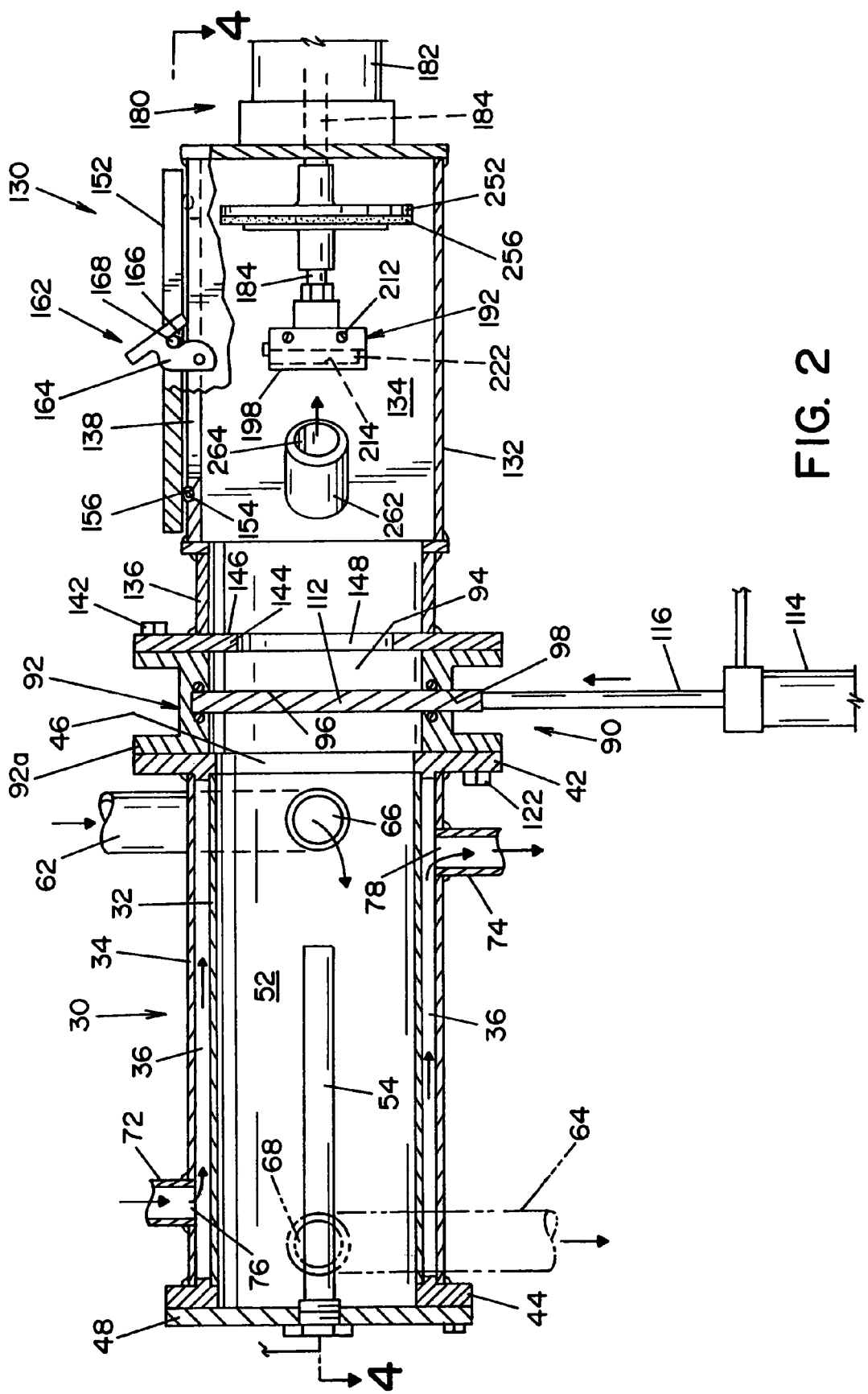
FIG. 2 is a cross-sectional view of the BIER vessel and indicator loading chamber of the system shown in FIG. 1, showing a slide gate in a closed position isolating the interior chamber of the BIER vessel from the loading chamber.
Figure 3:
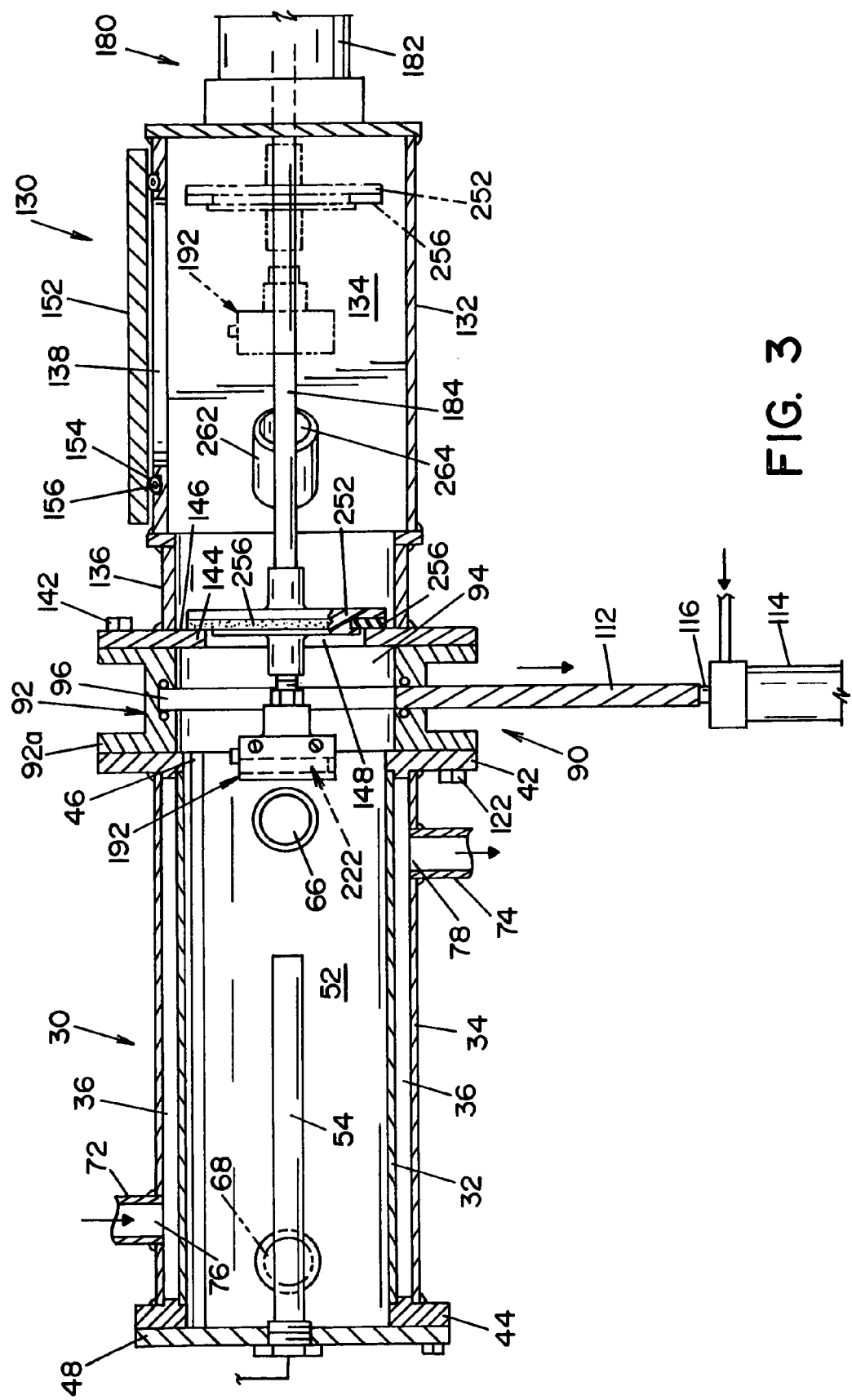
FIG. 3 is a cross-sectional view of a BIER vessel and an indicator loading chamber showing the slide gate in an opened position and an indicator moved into the inner chamber of the BIER vessel.
Figure 4:
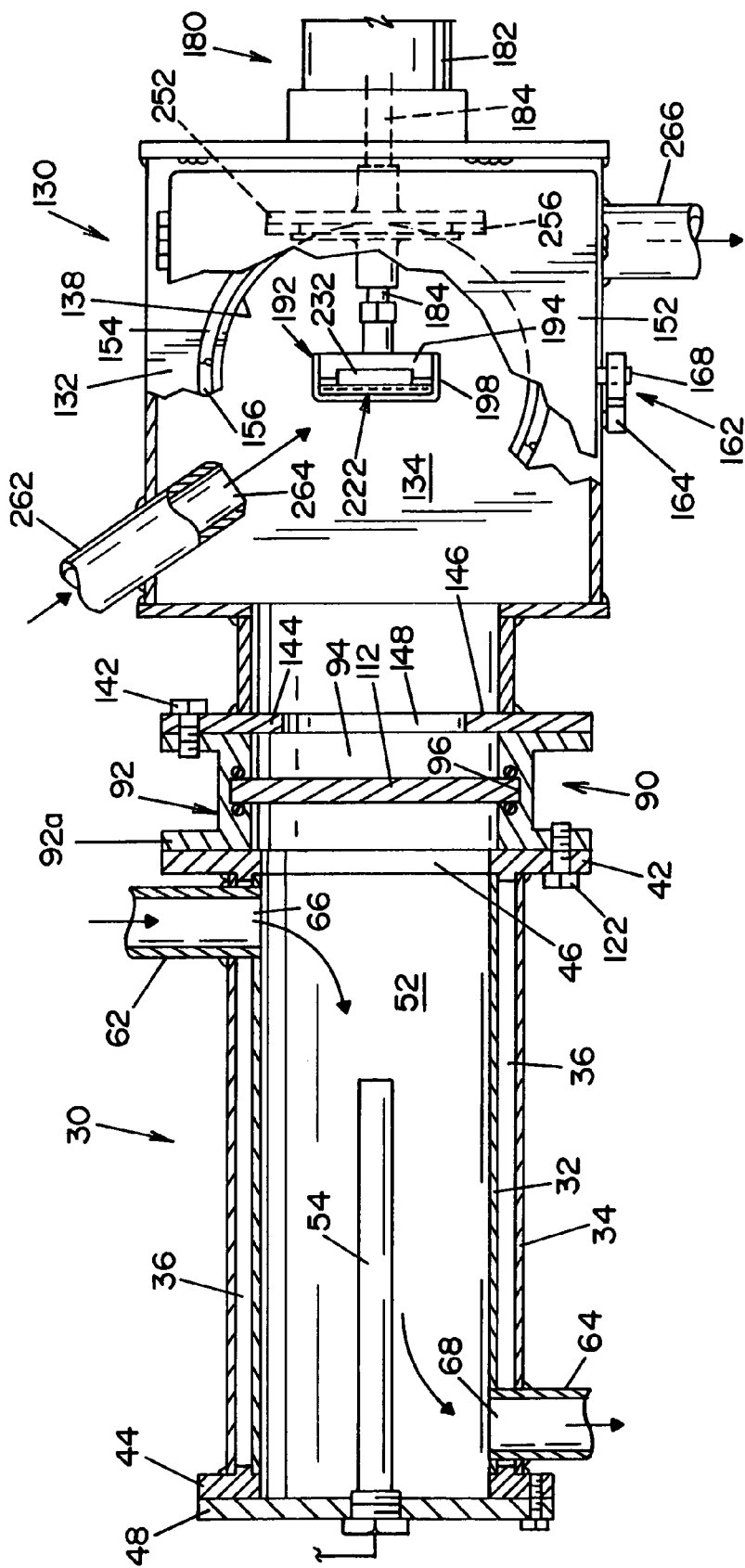
FIG. 4 is a partially sectioned view taken along lines 4-4 of FIG. 2.

The BIER vessel assembly 20, best seen in FIGS. 2-4, is comprised of a test vessel 30, a gate mechanism 90, an indicator loading assembly 130 and an indicator shuttle assembly 180. Test vessel 30 is comprised of an inner shell 32 and an outer jacket 34. Jacket 34 is dimensioned to be spaced-apart from shell 32 so as to define a cavity 36 therebetween. A front flange 42 and a back flange 44 are attached to the ends of shell 32 and jacket 34. Flanges 42, 44 are attached to shell 32 and jacket 34 to form a fluid-tight connection therewith. Front flange 42 is formed to define an opening 46, best seen in FIG. 2.

Figure 7:
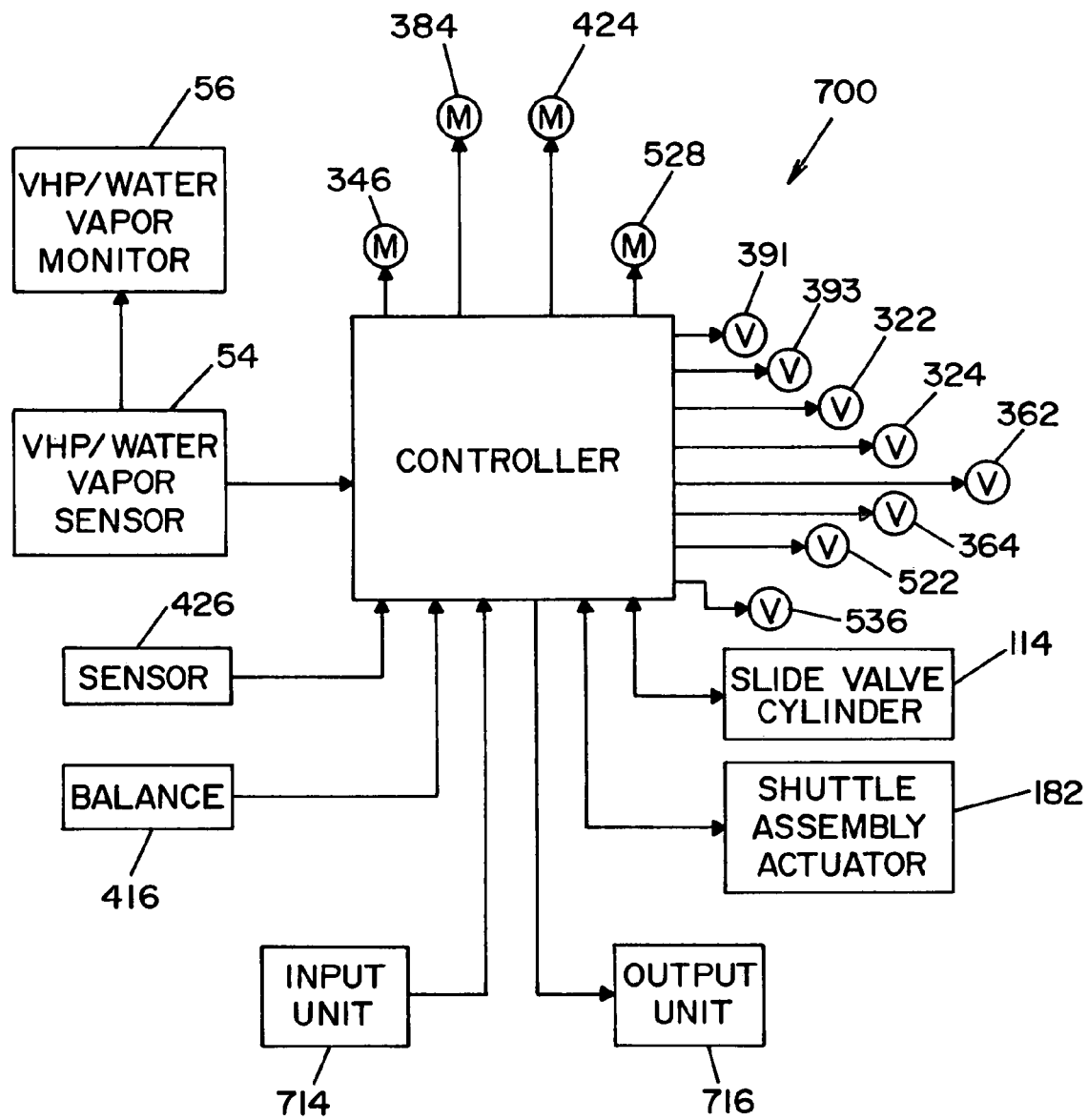
FIG. 7 is a schematic representation of a controlled system for the BIER vessel and high-speed biological indicator shuttle system shown in FIG. 1.
Figure 8:
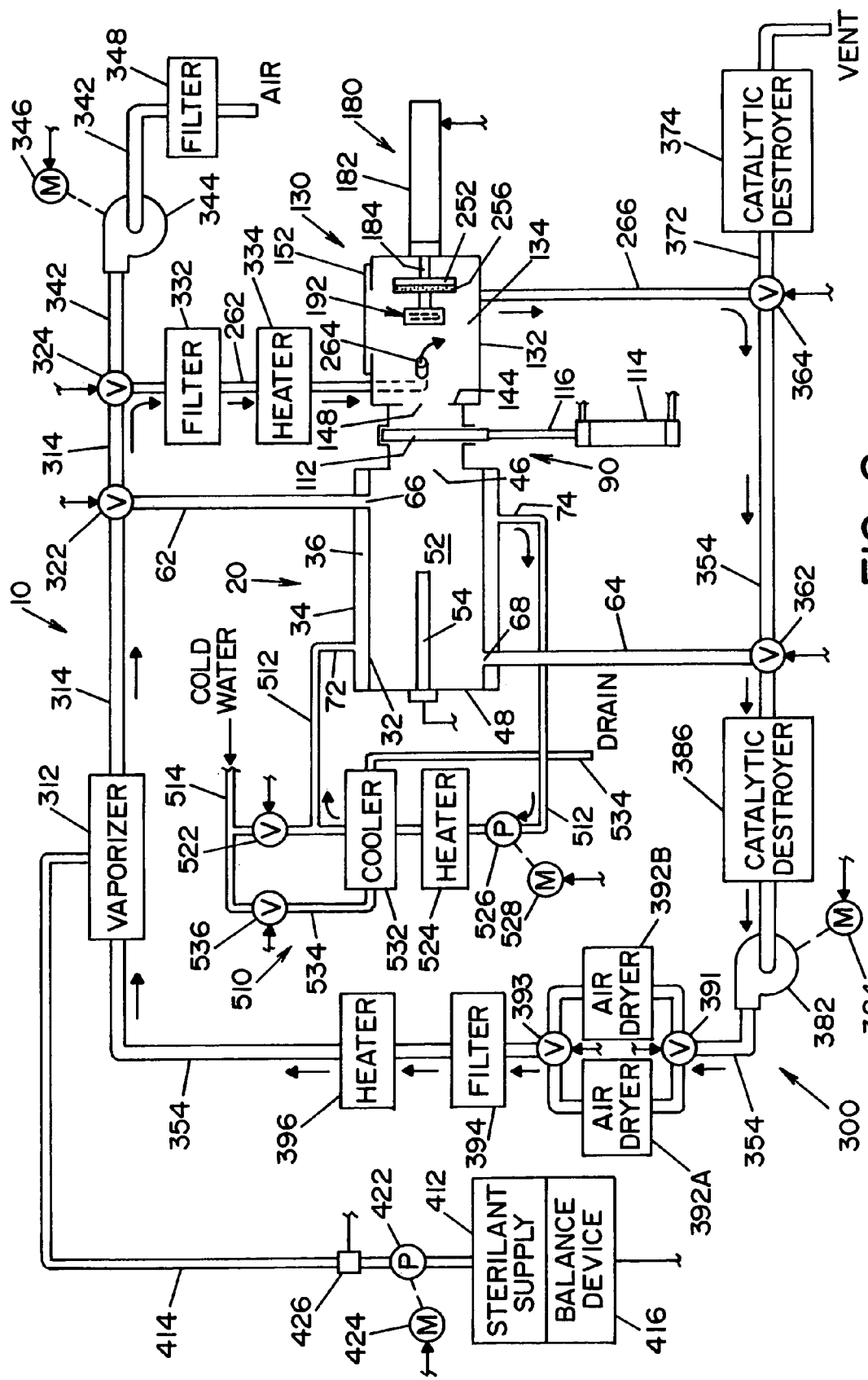
FIG. 8 is a schematic view of the BIER vessel and high-speed biological indicator shuttle system shown in FIG. 1 illustrating a pre-conditioning phase of an operating cycle of the system.

In the embodiment shown, shell 32 and jacket 34 are preferably cylindrical in shape, and along with end flanges 42, 44 are preferably formed of metal. In this respect, shell 32, jacket 34 and flanges 42, 44 are welded together. A plate 48 is attached to the back flange 44 to close one end of test vessel 30. Test vessel 30 defines a sterilization chamber 52. Plate 48 has an opening therethrough to receive a sensor 54 that extends into sterilization chamber 52, as best seen in FIGS. 2 and 3. In the embodiment shown, sensor 54 is a near infrared sensor that detects the concentration of sterilant and the concentration of water within sterilization chamber 52. A sensor manufactured by Guided Wave and sold under the trade designation $H_2O_2$ Vapor Monitor is illustrated in the embodiment shown. Sensor 54 is connected to a VHP/water vapor monitor 56, as schematically illustrated in FIG. 7, that is operable to calculate the dew point in sterilization chamber 52.

A vessel inlet line 62 and a vessel outlet line 64 communicate with sterilization chamber 52, as best seen in FIG. 2. Vessel inlet line 62 defines an inlet port 66, and vessel outlet line 64 defines an outlet port 68 to sterilization chamber 52.

Heating lines 72, 74 communicate with cavity 36 defined between shell 32 and jacket 34. Heating lines 72, 74 define heating fluid inlet port 76 and heating fluid outlet port 78.

As illustrated in the drawings, gate mechanism 90 is attached to test vessel 30. Gate mechanism 90 includes a flanged valve body 92. In the embodiment shown, flanged valve body 92 is cylindrical in shape and defines an interior opening 94 that is aligned with opening 46 in front flange 42 of test vessel 30. A slot 96, best seen in FIG. 4, is formed in the inner surface of flanged valve body 92. An opening 98 is formed through one side of valve body 92 to communicate with slot 96. A valve plate 112 extends through the opening in valve body 92 and is moveable within slot 96. Movement of valve plate 112 is controlled by a cylinder 114 having a cylinder rod 116 that is attached to valve plate 112. Cylinder 114 is operable to move valve plate 112 from a first position, as shown in FIG. 2, wherein valve plate 112 closes interior opening 94 in valve body 92 and forms a barrier to test vessel 30, and a second position, as shown in FIG. 3, wherein valve plate 112 is withdrawn from interior opening 94 in valve body 92. Gate mechanism 90 is fixedly secured to test vessel 30 by conventional fasteners 122 extending through a flange 92a on valve body 92 and front flange 42 on test vessel 30. A fluid-tight seal is formed by seal means (not shown) between test vessel 30 and gate mechanism 90.

Referring now to the indicator loading assembly 130, a housing 132 is disposed in alignment with test vessel 30 and valve body 92 of gate mechanism 90. In the embodiment shown, housing 132 is generally rectangular in shape and defines an inner loading chamber. One end of housing 132 is opened and includes a flanged collar 136. Flanged collar 136 extends toward test vessel 30 and provides means for attaching housing 132 to gate mechanism 90. Conventional fasteners 142 secure flanged collar 136 to valve body 92, as shown in the drawings. Inner loading chamber 134 communicates with interior opening 94 in valve body 92, when valve plate 112 is in its second position. Flanged collar 136 includes an inwardly extending wall 144 that defines an annular surface 146 that faces toward loading chamber 134. Wall 144 defines an opening 148 in flanged collar 136.

An opening 138 in the upper surface of housing 132 defines an access port that communicates with loading chamber 134. Opening 138 is dimensioned to facilitate insertion and removal of an indicator, as shall be described in greater detail below. A lid 152 is hinged to housing 132 to be moveable between a first position allowing access to loading chamber 134 and a second position closing access to loading chamber

134. A seal element 154, best seen in FIG. 2, is disposed within a slot 156 formed in housing 132 at a location beneath lid 152. Seal element 154 is operable to form a fluid-tight seal between lid 152 and housing 132 when lid 152 is in a closed position.

A latch assembly 162 is provided on housing 132 and lid 152 to secure lid 152 in a sealed, closed position. Latch assembly 162 includes a latch element 164 that is pivotally mounted to housing 132, as best seen in FIG. 2. Latch element 164 has a generally arcuate slot 166 formed therein. Slot 166 is dimensioned to capture a pin 168 extending from lid 152. A safety lock (not shown) is provided to ensure lid 152 is not opened during the cycle.

Figure 5:
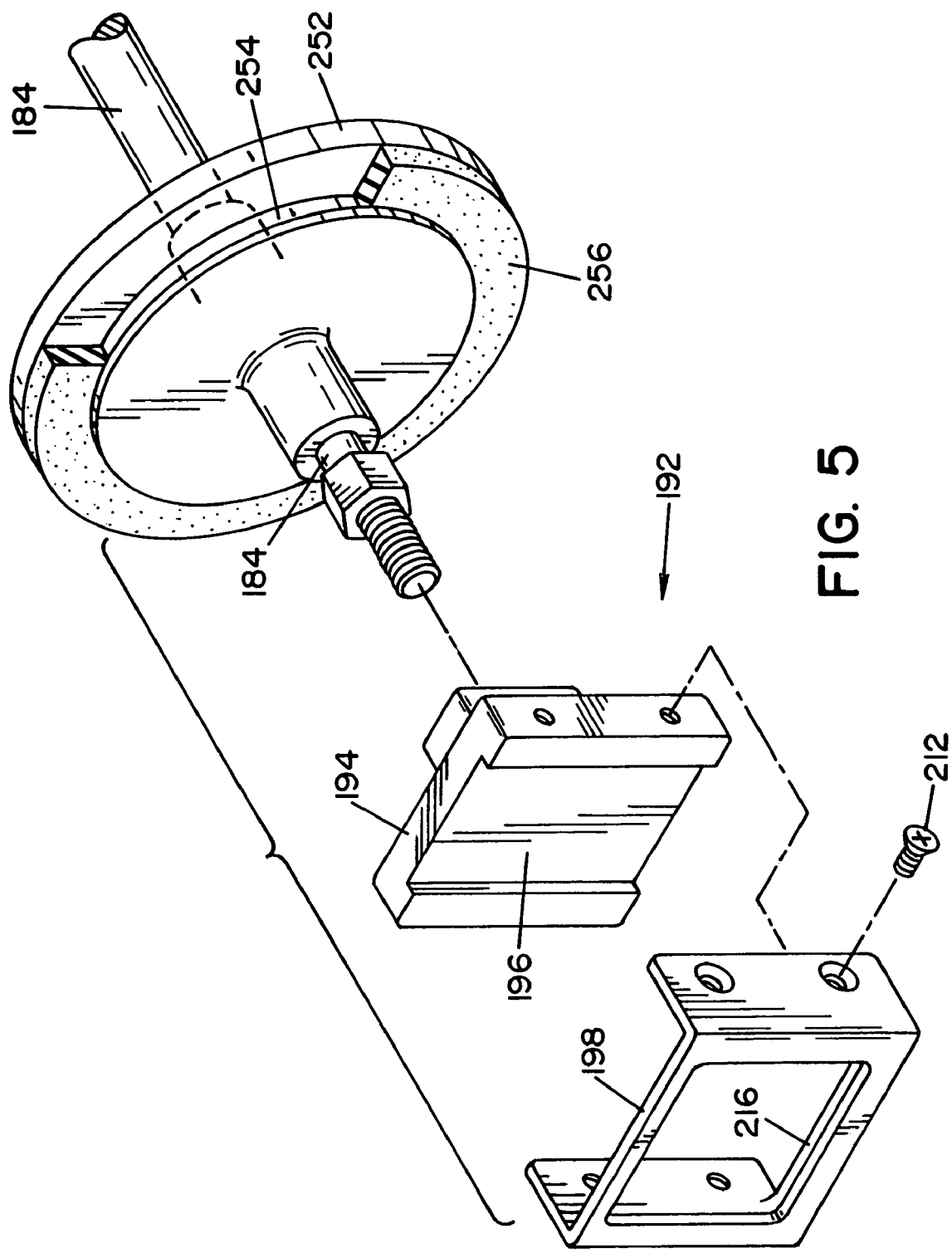
FIG. 5 is an exploded, perspective view of a shuttle assembly from the high-speed shuttle system.

Shuttle assembly 180 is mounted to the closed end of housing 132. Shuttle assembly 180 is comprised of an actuator 182 having an elongated rod 184 that is moveable axially into sterilization chamber 52 of test vessel 30. In the embodiment shown, actuator 182 is a high-speed linear actuator. In a preferred embodiment of the present invention, linear actuator 182 is manufactured by Exlar. Actuator rod 184 is moveable between a retracted position, as shown in FIG. 2, and an extended position, as shown in FIG. 3. A test sample holder 192 is mounted to the free end of actuator rod 184. In the embodiment shown, holder 192 is dimensioned to receive a case 222 that holds an indicator test panel or sheet 242, as will be described in more detail below. It is also contemplated that holder 192 may be designed to hold objects, such as by way of example and not limitation, a nut, such as an almond. In the embodiment shown, holder 192 is comprised of a bracket 194 that is threadingly attached to conventional screw threads that are formed on the end of actuator rod 184. A wide, rectangular recess 196 is formed in the front face of bracket 194. A generally U-shaped cover plate 198 is dimensioned to be attached to bracket 194 by conventional fasteners 212, as illustrated in FIG. 5. When cover plate 198 is attached to bracket 194, a rectangular slot 214 is defined between cover plate 198 and bracket 194. A lip or ledge 216, best seen in FIG. 5, is formed along the lower edge of cover plate 198 to define the bottom of slot 214.

Figure 6:
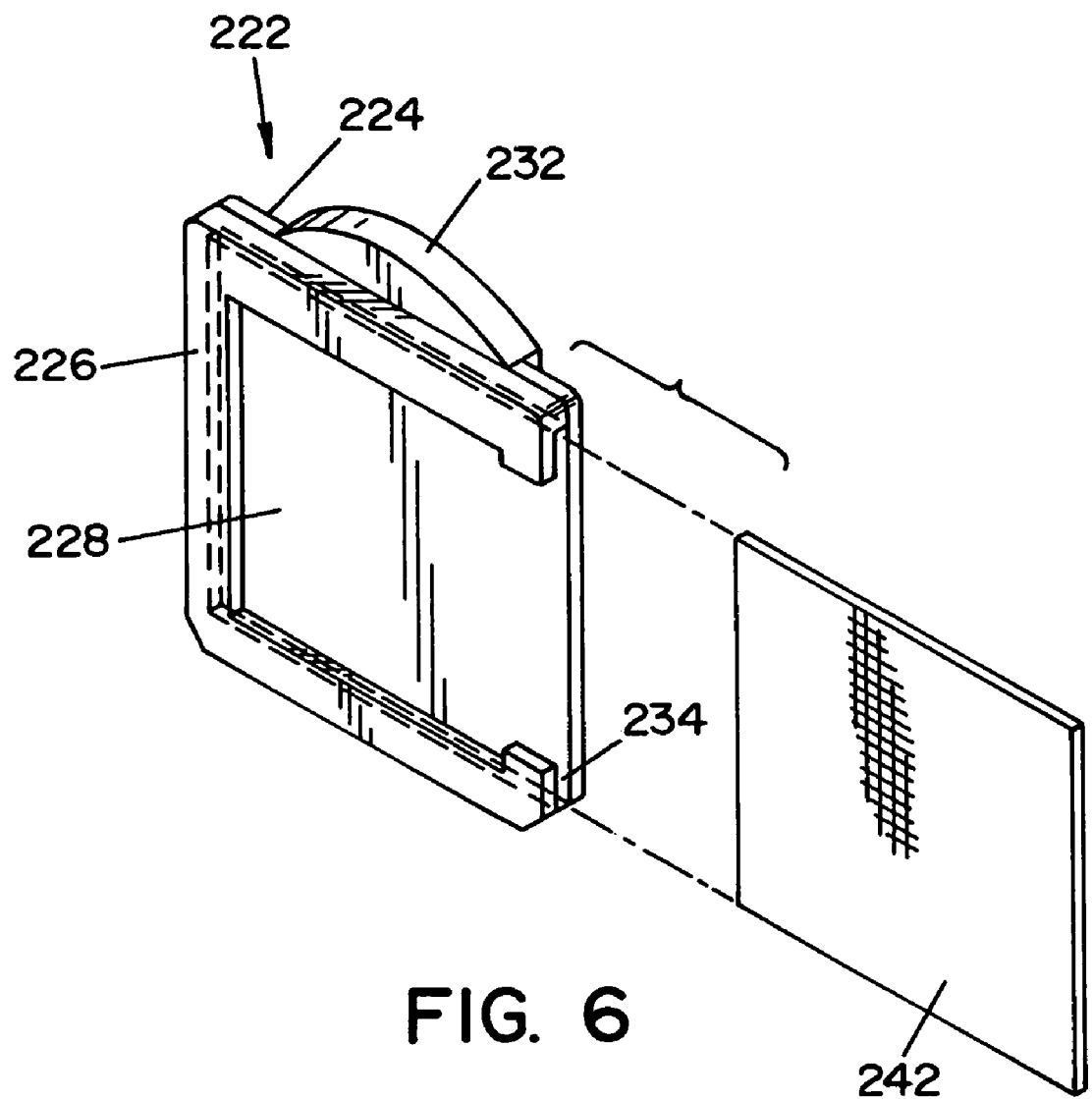
FIG. 6 is a perspective view of an indicator and a holder therefor that is used in the shuttle assembly shown in FIG. 5.

Referring now to FIG. 6, an indicator case 222 is shown. Case 222 is comprised of a flat, generally rectangular back panel 224 and a U-shaped front panel 226. In the embodiment shown, a generally rectangular opening 228 is formed in front panel 226. A round opening or oval opening is also contemplated. A tab 232 is formed on back panel 224. Front and back panels 226, 224 are attached to each other and define a slot 234 therebetween. Slot 234 extends through one edge of case 222, as illustrated in FIG. 6.

Case 222 is dimensioned to receive and hold an indicator test panel or sheet 242 containing a biological microorganism. Indicator panel or sheet 242 is dimensioned to slide within slot 234 of case 222, wherein a portion of indicator sheet 242 is exposed by opening 228 in front panel 226.

An outwardly extending collar 252 is mounted on actuator rod 184 adjacent indicator holder 192. Collar 252 is generally circular in shape and is dimensioned to be larger than opening 148 defined by inwardly extending wall 144 of flanged collar 136. Collar 252 is preferably formed of a polymeric material. An annular slot 254 is defined at the base of collar 252. Slot 254 is dimensioned to receive an annular seal element 256, best seen in FIG. 5. In a preferred embodiment, seal element 258 is formed of silicone and is dimensioned to abut annular surface 146 of wall 144 on flanged collar 136 and to form a seal therewith when actuator rod 184 is in an extended position, as illustrated in FIG. 3.

A housing inlet pipe 262 extends into loading chamber 134 of housing 132. Housing inlet pipe 262 defines an inlet port 264. Housing inlet pipe 262 is oriented such that inlet port 264 is directed toward first position of indicator holder assembly 192. A housing outlet pipe 266 is attached to housing 132 to define an outlet port 268 in loading chamber 134.

Referring now to FIG. 1, sterilant generating and circulating system 300 is best illustrated. In the embodiment shown, the sterilant generating and circulating system 300 is connected to test vessel 30 and indicator loading assembly. A vaporizer 312 (also referred to herein as a "generator") is connected to test vessel 30 and indicator-loading assembly 130 by means of a main sterilant supply line 314. Main sterilant supply line 314 is connected to vessel inlet line 62 and is connected to housing inlet pipe 262, as best seen in FIG. 1. A three-way valve 322 is disposed in main sterilant supply line 314 to control flow through main sterilant supply line 314 and vessel inlet line 62. Similarly, a three-way valve 324 is disposed in main sterilant supply line 314 to control fluid flow to housing inlet pipe 262. As seen in FIG. 1, a filter 332 and heater 334 are disposed within housing inlet pipe 262 between housing 132 and valve 324.

An air inlet line 342 communicates with valve 324. Air inlet line 342 terminates at an air source or atmosphere, as shown in FIG. 1. A blower 344 driven by a motor 346 is disposed within air inlet line 342 to blow air into housing 132, as shall be described in greater detail below. A filter 348 is disposed between blower 344 and the air source or atmosphere.

Sterilant generating and circulating system 300 includes a main return line 354 that connects test vessel 30 and housing 132 to vaporizer 312. Test vessel 30 is connected to return line 354 by vessel outlet line 64, and housing 132 is connected to return line 354 by housing outlet pipe 266. A three-way valve 362 is disposed in return line 354 where vessel outlet line 64 intersects return line 354 to control flow therethrough. A three-way valve 364 is disposed in main return line 354 where housing outlet pipe 266 intersects main return line 354, to control flow therethrough.

A vent line 372 that communicates with the atmosphere is connected to valve 364 where housing outlet pipe 266 intersects main return line 354. A catalytic destroyer 374 is disposed in vent line 372.

A blower 382, driven by a motor 384, is disposed within main return line 354 between valve 362 and vaporizer 312. Blower 382 is operable to circulate a sterilant and a carrier gas, i.e., air through the closed-loop sterilant generating and circulating system 300. A catalytic destroyer 386 is disposed in main return line 354 between blower 382 and valve 362, as illustrated in FIG. 1. Catalytic destroyer 386 is operable to break down vaporized hydrogen peroxide ($H_2O_2$) flowing therethrough, as is conventionally known. Catalytic destroyer 386 converts the vaporized hydrogen peroxide ($H_2O_2$) into water and oxygen. A pair of air dryers 392A and 392B are disposed within main return line 354 between blower 382 and vaporizer 312. Air dryers 392A, 392B are arranged to be parallel to each other. A first control valve 391 is disposed within main return line 354 upstream, i.e., before, air dryers 392A, 392B, and a second control valve 393 is disposed downstream, i.e., after, air dryers 392A, 392B in the direction of flow of the carrier gas. First and second control valves 391, 393 are operable to direct flow through one or the other of air dryers 392A, 392B. In this respect, airflow is directed through one air dryer while the other air dryer is regenerated. Air dryers 392A, 392B are operable to remove moisture from air blown through the closed loop system. A filter 394 and a heater 396 are disposed within main return line 354 between air dryers 392A, 392B and vaporizer 312. Filter 394 is operable to filter the air blown through main return line 354 by blower 382. Heater 396 is operable to heat air blown through main return line 354 by blower 382. In this respect, air circulating through main return line 354 is dried, filtered and is heated prior to the air entering vaporizer 312.

Vaporizer 312 is connected to a liquid sterilant supply 412 by a feed line 414. A conventionally known balance device 416 is associated with sterilant supply 412 to measure the actual mass of sterilant being supplied to vaporizer 312. A pump 422 driven by a motor 424 is provided to convey metered amounts of the liquid sterilant to vaporizer 312 where the sterilant is vaporized by conventionally known means. In an alternate embodiment, pump 422 is provided with an encoder (not shown) that allows monitoring of the amount of sterilant being metered to vaporizer 312. If an encoder is provided with pump 422, balance device 416 is not required.

Test vessel heating/cooling system 510 is attached to test vessel 30 to be in fluid communication with cavity 36 defined between jacket 34 and shell 32. In the embodiment shown, heating/cooling system 510 includes a conduit 512 that basically forms a closed-loop system. Heating/cooling system 510 is operable to circulate heated or cold fluid through cavity 36 defined between shell 32 and jacket 34 of test vessel 30. In this respect, conduit 512 is connected to input and output lines 72, 74 of test vessel 30 to define a closed-loop system. A water line 514 is connected to conduit 512 to provide cold water to heating/cooling system 510. A valve 522 controls the flow of water to heating/cooling system 510. A heater 524 is disposed within conduit 512. Heater 524 is operable to generate hot water within heating/cooling system 510. A pump 526, driven by a motor 528, circulates the steam through cavity 36 of test vessel 30. A cooler/chiller 532 is disposed around line 512 to cool water flowing through line 512. A branch line 534 from water line 514 provides the cooling water to cooler/chiller 532. Branch line 534 extends from cooler/chiller 532 to a drain, as illustrated in the drawings. A valve 536 controls flow through branch line 534.

Referring now to FIG. 7, a control system 700 for controlling the operation of system 10 is schematically illustrated. Control system 700 includes a controller 710 that is provided to control operations of motors 346, 384, 424, 528 and valves 322, 324, 362, 364. Controller 710 also monitors the vaporized hydrogen peroxide (VHP) sensor 54 as well as sensor 426 and balance system 416 that feed a sterilant to vaporizer 312. Controller 710 is a system microprocessor or a microcontroller that is programmed to control the operation of system 10. An input unit 714 is provided and attached to controller 710 to allow a user of system 10 to input operation parameters, as shall be described in greater detail below.

Input unit 714 may be any device that would facilitate the input of data and information to controller 710 by a user of system 10, such as by way of example and not limitation, a keypad, a keyboard, a touch screen or switches. An output unit 716 is also connected to controller 710. Output unit 716 is provided to enable controller 710 to provide information to the user on the operation of system 10. Output unit 716 may be, by way of example and not limitation, a printer, display screen or LED display.

Controller 710 is programmed such that system 10 operates in certain operating modes. In a preferred embodiment of the present invention, controller 710 is programmed to include the following operating modes:

Standby Mode
Ready Mode
Decontaminate Loading Chamber Mode
Aeration of Loading Chamber Mode
Test Vessel Temperature Mode
Leak Test and Sensor Check Mode
Charge Test Vessel Mode
Install Indicator Mode
Expose Indicator Mode
Aerate Indicator Mode
Aerate Test Vessel Mode
Remove Indicator Mode
Standby Mode Initially, system 10 is configured with actuator rod 184 in a retracted position, as illustrated in FIG. 2 and with valve plate 112 of gate mechanism 90 in its first position separating and isolating loading chamber 134 of housing 132 from sterilization chamber 52 of test vessel 30. Vaporizer 312 and motors 346, 384, 424, 528 are not operating.

During the Standby Mode, controller 710 shuts off all components of system 10 and displays the term "standby" on an output unit 716. During this mode of operation, the operative components of system 10 are basically inactive.

Ready Mode

Controller 710 waits for input data from a user with respect to an operation desired. System 10 is designed to receive a plurality of input parameters from a user by means of input unit 714. Such input parameters may include, by way of example and not limitation, (1) the operating temperature of the test vessel, (2) the desired saturation level (in percent) of the sterilant to be used, (3) the indicator exposure time (in seconds), (4) the air flow rate into the loading chamber, and the like.

Decontaminate Loading Chamber Mode

Prior to testing an indicator sheet 242, loading chamber 134 of housing 132 is decontaminated. Controller 710 causes valves 322, 324, 362 and 364 to establish a first closed-loop sterilant circulation path through loading chamber 134 of housing 132. Specifically, controller 710 moves valves 322, 362 to a position allowing flow through main supply line 314 and main return line 354 respectfully, but isolating, i.e., blocking, flow into test vessel 30. At the same time, controller 710 operates valves 324, 364 to open a fluid path through loading chamber 134, but blocking flow to or from air inlet line 342 and vent line 372. Controller 710 causes motor 384 to initiate blower 382 to circulate a carrier gas through a first closed-loop sterilant circulation path defined by main sterilant supply line 314, housing inlet pipe 262, loading chamber 134, housing outlet pipe 266 and main return line 354. In the embodiment shown, the carrier gas is air. Controller 710 causes sterilant to be supplied to vaporizer 312 to generate vaporized hydrogen peroxide. The vaporized hydrogen peroxide is carried through main sterilant supply line 314 to housing inlet pipe 262 into loading chamber 134 to sterilize the interior thereof as well as indicator holder 192 and actuator rod 184. As will be appreciated, lid 152 to housing 132 is in a closed position. Sensors (not shown) may be provided to insure that lid 152 on housing 132 is in a closed position prior to circulation of the sterilant therethrough.

The foregoing procedure describes one procedure for decontaminating loading chamber 134. Another procedure for decontaminating loading chamber 134 is to move valve plate 112 to its second position wherein valve plate 112 is withdrawn from interior opening 94 in valve body 92, thereby allowing loading chamber 134 to communicate with sterilization chamber 52. Valve 364 is moved to a position preventing flow through housing outlet pipe 266, and valve 362 is moved to a position allowing flow through outlet line 64 from test vessel 30 to return line 354. Thus, sterilant flowing into loading chamber 134 is directed to sterilization chamber 52, and then back to return line 354. Such a procedure allows sensor 54 to monitor the sterilant concentration during decontamination of loading chamber 134.

Aeration of Loading Chamber Mode

After a predetermined period of time, motor 424 is shut off by controller 710 to shut off the flow of sterilant to vaporizer 312. Motor 384 and blower 382 continue to operate to circulate air through vaporizer 312 and along the first closed-loop path through loading chamber 134 of housing 132. As the vaporized hydrogen peroxide exits housing 132, it enters catalytic destroyer 386 via main return line 354 wherein the vaporized hydrogen peroxide is destroyed, i.e., breaks down, into oxygen and water. Blower 382 is continuously run for a predetermined period of time to insure the entire amount of vaporized hydrogen peroxide within sterilant generating and circulating system 300 and housing 132 is broken down by catalytic destroyer 386.

Test Vessel Temperature Mode

Based upon the desired operating temperature of test vessel 30, as inputted by the user, controller 710 causes heating/cooling system 510 to be energized. In this respect, motor 528 is energized to drive pump 526 that in turn pumps water within heating/cooling system 510 through cavity 36 around test vessel 30. Heater 524 is energized to heat the water circulating through heating/cooling system 510 and cavity 36 to a desired, user-inputted temperature. A sensor (not shown) indicates when the temperature of test vessel 30 is at the desired, user-inputted, temperature. It will be appreciated that since vessel-heating/cooling system 510 is separate and independent of sterilant generating and circulating system 300, the Test Vessel Temperature Mode may run separately and independently from other operating modes described herein.

Leak Test and Sensor Check Mode

A leak test is preferably performed along system 10 to determine that there are no leaks therein. At the same time, a sensor check may be performed to determine that sensors 54 and 426 are operating properly.

Charge Test Vessel Mode

Based upon the desired concentration of vaporized hydrogen peroxide (VHP) to be established within test vessel 30, as inputted by a user, controller 710 causes valves 322, 324, 362, 364 to move to positions wherein a second closed-loop sterilant flow path is established through test vessel 30. More specifically, the dew point within sterilization chamber 52 is calculated from the temperature, vaporized hydrogen peroxide and water concentration within sterilization chamber 52. In this respect, valves 322 and 362 are moved to positions wherein main sterilant supply line 314 and main return line 354 of sterilant generating and circulating system 300 communicates with vessel inlet line 62 and outlet line 64, respectively. Vaporizer 312 is then energized by controller 710. Motor 424 that is connected to pump 422 is actuated to cause sterilant to flow to vaporizer 312 from sterilant supply 412. In a conventionally known manner, the liquid hydrogen peroxide is converted into vaporized hydrogen peroxide in vaporizer 312. The vaporized hydrogen peroxide is circulated through test vessel 30 by blower 382. Based upon signals from sensor 426, controller 710 monitors the amount of vaporized hydrogen peroxide provided to vaporizer 312. Sensor 54 within sterilization chamber 52 provides signals to controller 710 as to the concentration of vaporized hydrogen peroxide within chamber 52. When the conditions within sterilization chamber 52 are at the user-inputted desired level, chamber 52 is ready for a test cycle.

Blower 382 continuously circulates a carrier gas (air) that carries the vaporized hydrogen peroxide from vaporizer 312 into and through sterilization chamber 52. Vaporized hydrogen peroxide exiting chamber 52 through vessel outlet line 64 and main return line 354 flows through catalytic destroyer 386 where it is broken down into oxygen and water.

Install Indicator Mode

When the parameters (i.e., temperature and concentration of vaporized hydrogen peroxide) within test vessel 30 are at the desired user's input levels, indicator sheet 242 may be installed in indicator holder 192 within loading chamber 134. To insert indicator sheet 242 in indicator holder 192, latch assembly 162 is moved to allow lid 152 to be opened. A biological indicator sheet 242 (or other indicators) within case 222 is then placed within recess 196 within indicator holder 192. Indicator sheet 242 is arranged such that the face of indicator sheet 242 is exposed through the opening in holder 192. Lid 152 to housing 132 is then closed and latch assembly 162 is secured, thereby sealing the same.

Expose Indicator Mode

Figure 9:
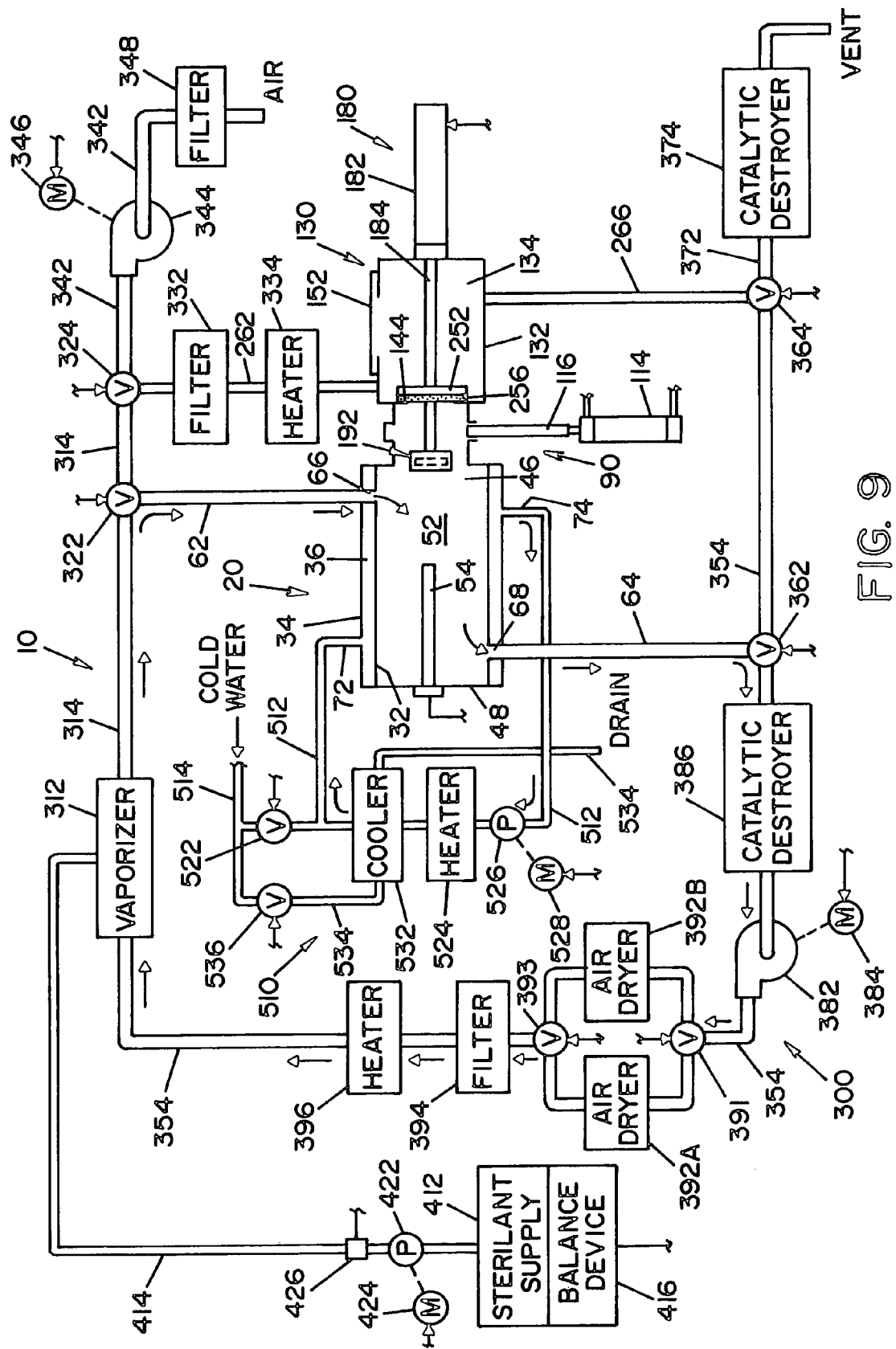
FIG. 9 is a schematic view of the BIER vessel and high-speed biological indicator shuttle system of FIG. 1 illustrating an indicator exposure phase of the operating cycle of the system.

With indicator sheet 242 mounted on holder 192, controller 710 causes indicator sheet 242 to be exposed to the conditions within test vessel 30 in accordance with user-inputted data. In this respect, controller 710 causes valve plate 112, that isolates sterilization chamber 52 from loading chamber 134, to be moved to its second position wherein sterilization chamber 52 communicates with loading chamber 134 via the interior opening 94 of valve body 92. Once valve plate 112 has moved to its second, i.e., opened, position, controller 710 causes actuator 182 to move actuator rod 184 to its extended position, wherein holder 192 is moved into sterilization chamber 52. FIG. 9 illustrates the instance when biological indicator sheet 242 on holder 192 is within sterilization chamber 52 and exposed to the vaporized hydrogen peroxide flowing therethrough. As indicated in FIG. 9, seal element 256 on collar 252 on actuator rod 184 seals opening 148 defined by wall 144 of flanged collar 136 thereby maintaining the original conditions within test chamber 52.

It should be pointed out that linear actuator 182 moves at a rapid speed such that indicator sheet 242 travels from the sterile conditions within loading chamber 134 to sterilization chamber 52 within a fraction of a second. In a preferred embodiment, the travel time of indicator holder 192 from loading chamber 134 to the position in sterilization chamber 52, shown in FIG. 9, is a fraction of a second. As indicated above, the user would input the desired exposure time of indicator sheet 242 to the sterilant conditions within sterilization chamber 52. Because of the rapid movement and speed of linear actuator 182, exposure times to the sterilant conditions within sterilization chamber 52 may be extremely short, namely less than a second. In this respect, controller 710 would cause actuator 182 to drive holder 192 into test chamber 52 for a short duration, and then controller 710 would cause actuator 182 to reverse direction thereby removing holder 192 and indicator sheet 242 from sterilization chamber 52.

Upon removal of holder 192, valve plate 112 returns to its first position thereby sealing sterilization chamber 52 and isolating sterilization chamber 52 from loading chamber 134.

Aerate Indicator Mode

Figure 10:
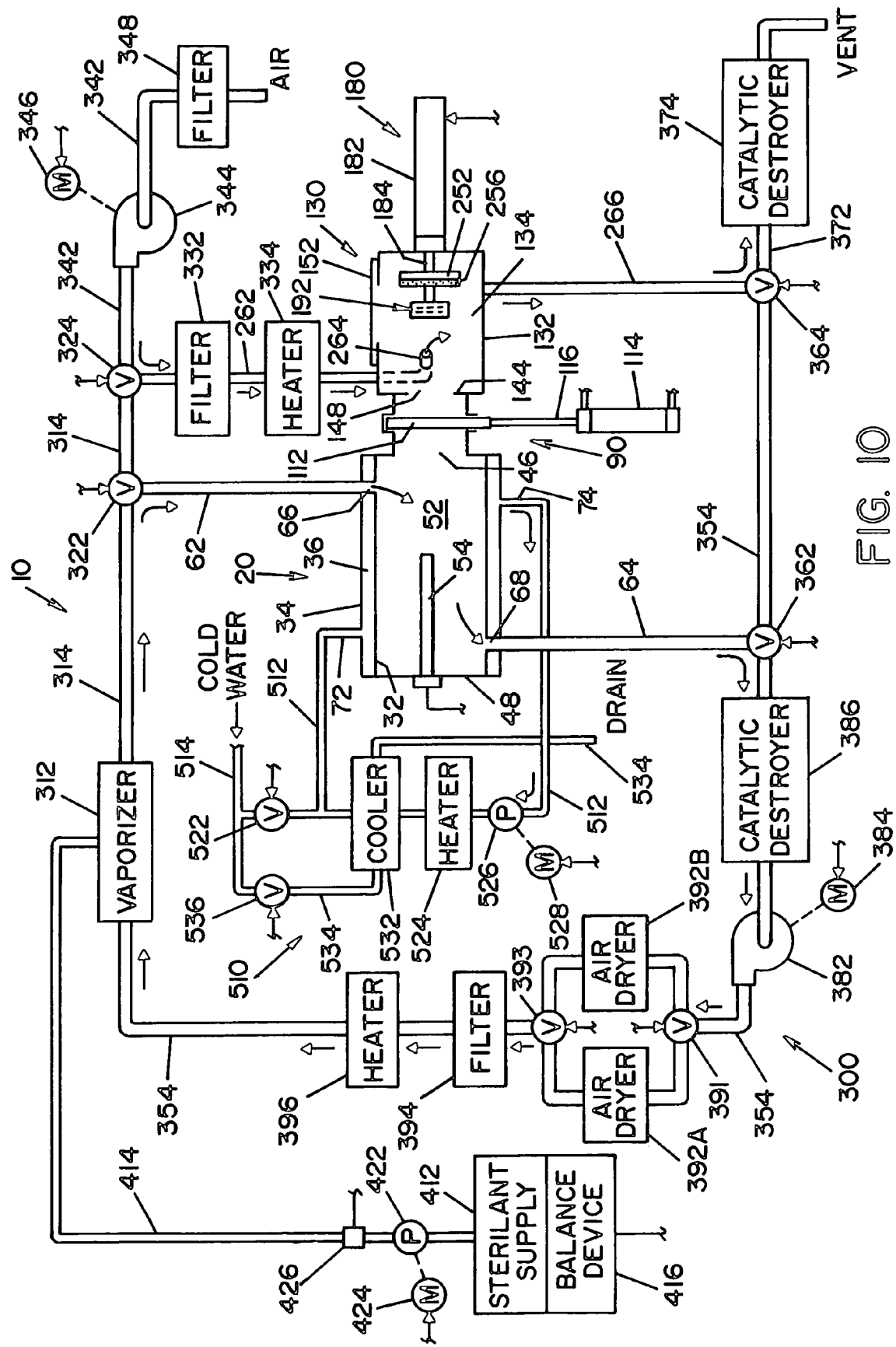
FIG. 10 is a schematic view of the BIER vessel and high-speed biological indicator shuttle system of FIG. 1 illustrating an aeration phase of the operating cycle of the system.

Prior to exposing indicator sheet 242 to the conditions within sterilization chamber 52 (or immediately after the exposure), indicator sheet 242 and holder 192 are aerated to remove any residual sterilants or vapors from the vicinity of indicator sheet 242. In this respect, controller 710 energizes motor 346 causing blower 344 in air inlet line 342 to blow air into housing 132. Valves 324 and 364 are moved to positions that prevent flow to main sterilant supply line 314 and main return line 354, but allow the air from blower 344 to be directed through filter 332 and heater 334 in housing inlet pipe 262 and into loading chamber 134, as schematically illustrated in FIG. 10. In this respect, FIG. 10 shows the position of indicator sheet 242 immediately after the exposure to sterilization chamber 52. FIG. 10 shows valve plate 112 return to its initial position isolating sterilization chamber 52 from loading chamber 134. Clean, dry, heated air from blower 344 is directed over indicator sheet 242 to remove any residual vaporized hydrogen peroxide that may be in the vicinity of indicator sheet 242, and that may affect same. The air exits housing 132 through housing outlet pipe 266 and is directed by a valve to vent line 372. Catalytic destroyer 374 within vent line 372 destroys any residual vaporized hydrogen peroxide that may exist within loading chamber 134.

Aerate Test Vessel Mode

While loading chamber 134 and indicator holder 192 are being aerated, sterilization chamber 52 within test vessel 30 may likewise be aerated. Controller 710 causes vaporizer 312 to shut down thereby preventing any additional vaporized hydrogen peroxide from being formed. Blower 382 continues to operate thereby circulating air through the closed-loop second path shown in FIG. 10. As air continues to circulate through the closed-loop system, vaporized hydrogen peroxide (VHP) within sterilization chamber 52 of test vessel 30 is carried to catalytic destroyer 386 that breaks down the vaporized hydrogen peroxide within the system. After a predetermined period of time, all of the vaporized hydrogen peroxide within the system is broken down by catalytic destroyer 386. Controller 710 then causes motor 384 to shut down preventing further flow of air through the system.

Remove Indicator Mode

After a predetermined period of time of air being blown through loading chamber 134 of housing 132, controller 710 causes motor 346 to shut down blower 344 thereby stopping the flow of air into loading chamber 134. Loading chamber 134 may then be opened by releasing latch assembly 162 and opening lid 152, and removing case 222 and indicator sheet 242 therefrom. Indicator sheet 242 then undergoes conventionally known assaying procedures to test for the D values of the sterilant conditions within sterilization chamber 52 of test vessel 30.

The foregoing operating modes describe preferred modes for operating system 10. As will be appreciated, certain operating modes may be run simultaneously, and the operation of system 10 is not limited to the order of operation set forth above.

The present invention thus provides a BIER vessel system that minimizes or eliminates the transient portion of the exposure of indicator sheet 242 to a sterilant. High-speed linear actuator 182 and gate mechanism 90 allow indicator sheet 242 to be exposed to the sterilant for short time intervals. Linear actuator 182 likewise facilitates exact positioning and monitoring of the location of indicator sheet 242 relative to sterilization chamber 52, thereby enabling more accurate exposure time determinations and evaluation of the effects of the sterilant on indicator sheet 242.

The foregoing description is a specific embodiment of the present invention. It should be appreciated that this embodiment is described for purposes of illustration only, and that numerous alterations and modifications may be practiced by those skilled in the art without departing from the spirit and scope of the invention. For example, although the present invention has been described for test indicators exposed to vaporized hydrogen peroxide (VHP), it will be appreciated that the apparatus shown may be used with other types of sterilants, such as other vaporized peroxy compounds, ozone ethylene oxide and halogenated gases including gases that contain bromine and chlorine. It is intended that all such modifications and alterations be included insofar as they come within the scope of the invention as claimed or the equivalents thereof.

Having described the invention, the following is claimed:

1. An apparatus for testing the efficacy of a sterilant vapor, comprising:
   a test chamber having an inlet port and an outlet port;
   an indicator-loading chamber adjacent and connected to said test chamber, said loading chamber having an inlet port and an outlet port;
   a movable valve element disposed between said test chamber and said loading chamber, said valve element movable between a first position isolating said test chamber from said loading chamber and a second position opening said test chamber to said loading chamber;
   an indicator holder;
   means for reciprocally moving said indicator holder between a loading position in said loading chamber and a test position in said test chamber;
   a supply system connected to said inlet port and said outlet port of said test chamber and to said inlet port and said outlet port of said loading chamber wherein said supply system is operable to selectively flow a sterilant vapor and a purging gas through said test chamber and said loading chamber; and
   a controller operable to cause said valve element to move from said first position to said second position and said moving means to move said indicator holder to said test position for a predetermined period of time and to move said valve element to said first position when said indicator holder is in said loading position.

2. An apparatus as defined in claim 1, wherein said sterilant vapor is a multicomponent vapor containing a concentration of a sterilant vapor and a concentration of at least one other vapor.

3. An apparatus as defined in claim 2, wherein said sterilant vapor is hydrogen peroxide vapor and said at least one other vapor is water.

4. An apparatus as defined in claim 3, wherein said source of multicomponent vapor is a vaporizer, and said multicomponent vapor is vaporized from an aqueous mixture of hydrogen peroxide.

5. An apparatus as defined in claim 4, wherein said aqueous solution of hydrogen peroxide contains 3 to 98 percent hydrogen peroxide by weight.

6. An apparatus as defined in claim 4, wherein said aqueous solution of hydrogen peroxide contains 30 to 35 percent hydrogen peroxide by weight.

7. An apparatus as defined in claim 1, wherein said system for providing a sterilant vapor is a closed loop system.

8. An apparatus as defined in claim 1, wherein said purge gas is air.

9. An apparatus as defined in claim 1, wherein said means for reciprocally moving is a linear actuator.

10. An apparatus for testing the efficacy of a sterilizing environment on a test indicator, comprising:
    a test chamber having an inlet port and an outlet port;
    a loading chamber adjacent to said test chamber, said loading chamber having an inlet port and an outlet port;
    an opening connecting said test chamber to said loading chamber;
    a movable gate mechanism having a first position closing said opening and isolating said test chamber from said loading chamber, and a second position wherein said opening connects said test chamber to said loading chamber;

a system connected to said inlet port and said outlet port of said test chamber and to said inlet port and said outlet port of said loading chamber wherein said system is operable to selectively flow a sterilant vapor and a purging gas through said test chamber and through said loading chamber; and an indicator holder operable to move a test indicator from said loading chamber into and out of said test chamber when said gate mechanism is in said second position.

11. An apparatus as defined in claim 10, wherein said sterilant system is a closed loop system having a first path through said test chamber.

12. An apparatus as defined in claim 11, wherein said sterilant system includes a second path through said loading chamber.

13. An apparatus as defined in claim 12, wherein said indicator holder is movable along an axis through said loading chamber and said test chamber.

14. An apparatus as defined in claim 13, further comprising a shuttle assembly for moving said indicator holder between said loading chamber and said test chamber.

15. An apparatus as defined in claim 14, wherein said shuttle assembly includes a linear actuator.

16. An apparatus as defined in claim 10, wherein said system includes a blower operable to blow air though said loading chamber.

17. An apparatus as defined in claim 10, further comprising a linear actuator operable to move said indicator holder into and out of said test chamber.

18. An apparatus for testing the efficacy of a sterilizing environment on a test indicator, comprising:

a vessel having a sterilization chamber, an inlet port and an outlet port;

a housing having a loading chamber, an inlet port and an outlet port, said housing being adjacent to said vessel;

a passage connecting said sterilization chamber to said loading chamber;

a movable gate mechanism having a first position closing said passage and isolating said test chamber from said loading chamber, and a second position wherein said passage connects said test chamber to said loading chamber;

an indicator holder operable to move a test indicator from said loading chamber into and out of said test chamber when said gate mechanism is in said second position; and a circulation system for supplying a sterilant vapor and a purging gas, said circulation system connected to said inlet port and said outlet port of said vessel and to said inlet port and said outlet port of said housing, wherein said system is operable to selectively control the flow of said sterilant vapor and said purge gas through said sterilization chamber and said loading chamber.

19. An apparatus as defined in claim 18, wherein said shuttle assembly includes a linear actuator.

20. An apparatus as defined in claim 18, wherein said purging gas is air.

* * * * *